(12) United States Patent
Bilbeny Lojo et al.

(10) Patent No.: US 7,232,846 B2
(45) Date of Patent: Jun. 19, 2007

(54) AMINES AS ANTI-ALCOHOLISM AGENTS

(75) Inventors: Norberto Bilbeny Lojo, Santiago de Chile (CL); Hernan Garcia Madrid, Santiago de Chile (CL)

(73) Assignee: Garbil Pharma Investigacion Chile Ltda., Santiago de Chile ( * ) Notice: Subject to any disclaimer, the term of this patent is extended or adjusted under 35 U.S.C. 154(b) by 326 days.

(21) Appl. No.: 10/489,251

(22) PCT Filed: Sep. 19, 2002

(86) PCT No.: PCT/ES02/00442

§ 371 (c)(1),
(2), (4) Date: Mar. 11, 2004

(87) PCT Pub. No.: WO03/026634

PCT Pub. Date: Apr. 3, 2003

(65) Prior Publication Data

US 2004/0242701 A1 Dec. 2, 2004

(30) Foreign Application Priority Data

Sep. 24, 2001 (ES) ................................ 200102126

(51) Int. Cl.
*A61K 31/13* (2006.01)
(52) U.S. Cl. ..................................... 514/673; 514/674
(58) Field of Classification Search ................ 514/673, 514/674

See application file for complete search history.

(56) References Cited

FOREIGN PATENT DOCUMENTS

WO   WO 99/48500   *   9/1999
WO   WO 9948500       9/1999

OTHER PUBLICATIONS

Diehl, A. M. et al., "Supplemental putrescine reverses ethanol-associated inhibition of liver regeneration", abstract of Hepatology vol. 12, No. 4, pp. 633-637, 1990.*
Webster's II, New Riverside University Dictionary, 1988, pp. 933 and 944.*
Bergeron et al, "Polyamine Analog Regulation of NMDA Binding: A Structure-Activity Study", Abstract No. 713061 (1996).
Littleton et al, "Role of Polyamines and NMDA Receptors in Ethanol Dependence and Withdrawal", Abstract No. 200100296358 (May 2001).
Prendergast et al, "In Vitro Effects of Ethanol Withdrawal and Spermidine on Viability of HippoCampus from Male and Female Rat", Abstract No. 20010055610 (Dec. 2000).
Davidson et al, "Chronic Ethanol Treatment Leads to Increased Ornithine Decarboxylase Activity: Implications for a Role of Polyamines in Ethanol Dependence and Withdrawal", Abstract No. 199800501861 (Sep. 1998).

* cited by examiner

*Primary Examiner*—Brian Kwon
(74) *Attorney, Agent, or Firm*—Sughrue Mion, PLLC

(57) ABSTRACT

The oral administration to genetically alcoholic rats (from the strain UChB of the University of Chile) of a compound selected from endogenic polyamines (putrescine, spermidine, spermine), 1,3-propanediamine, their pharmaceutically acceptable salts and solvates, and their bioprecursor amides, causes a significant reduction in the alcohol consumption. The activity lasts for some time after the treatment period. Besides, there is a virtually null disulfiram-like adverse effect, what constitutes an advantage over the unpleasant use of some anti-alcoholism agents, such as calcium cyanamide or disulfiram itself. Therefore, the compounds of the invention are useful for the preparation of medicaments for the therapeutic and/or prophylactic treatment of alcoholism in human beings.

11 Claims, No Drawings

AMINES AS ANTI-ALCOHOLISM AGENTS

CROSS-REFERENCE TO RELATED APPLICATIONS

This Application is a 371 of PCT/ES02/00442, filed Sep. 19, 2002; the disclosure of which is incorporated herein by reference.

This invention relates to the use of chemically-known compounds for preparing pharmaceutical compositions for the treatment of alcoholism.

BACKGROUND ART

The expression "treatment of alcoholism" comprises the reduction of the desire for and habit of consuming alcoholic drinks, the treatment of alcohol dependence and the treatment of abstinence syndrome. Alcoholism may be viewed as a disease, a drug addiction, a learned response to crisis, a symptom of an underlying psychological or physical disorder, or a combination of these factors. Most approaches to the treatment of alcoholism require the alcoholic person to recognize his/her illness and to abstain from alcohol. Treatment programs then vary according to the accepted definition and theory of cause of alcoholism. Treatment types include combinations of: psychological rehabilitative treatments; organized self-help groups; aversion therapy based on behavior modification; injections of vitamins or hormones, and the use of abstinence-maintaining drugs. The present invention relates to the latter type of treatments.

One of the drug treatments of alcoholism, initiated in 1948 by Eric Jacobsen of Denmark, uses disulfiram (tetraethylthiuram disulfide), of formula $Et_2N-C(=S)-S-S-C(=S)-NEt_2$. The usual technique is to administer half a gram in tablet form daily for a few days; then, under carefully controlled conditions and with medical supervision, the patient is given a small drink of an alcoholic beverage. The presence of disulfiram in the drinker's body causes a reaction of hot flushing, nausea, vomiting, a sudden sharp drop of blood pressure, pounding of the heart, and even a feeling of impending death. These symptoms, usually known as "acetaldehyde syndrome" or "efecto adverso tipo-disulfiiram", result from an accumulation of the highly toxic first product of alcohol metabolism, acetaldehyde. Normally, as alcohol is converted to acetaldehyde, the latter is rapidly converted, in turn, to other harmless metabolites; but in the presence of disulfiram—itself non-toxic, although not completely innocuous—the metabolism of acetaldehyde is blocked, with the resulting toxic symptoms. The patient is thus dramatically shown the danger of attempting to drink while under disulfiram medication. A smaller daily dose of disulfiram is then prescribed, and the dread of the consequences of drinking acts as a chemical fence to prevent the patient from drinking as long as he continues taking the drug.

Besides being quite unpleasant for patients, treatment of alcoholism with disulfiram involves a high risk, because subjects treated with disulfiram suffer from very serious symptoms deriving from the ingestion of even small doses of alcohol. Thus, following disulfiram treatment cases of respiratory depression, cardiovascular collapse, cardiac arrhythmia, myocardium infarct, and sudden or unexpected death have occurred.

Citrated calcium cyanamide (two parts of citric acid by weight to one part of CaNCN) is another drug used as anti-alcoholism agent, which has a disulfiram-like mechanism of action. It is preferred by some therapists because the reaction with alcohol is milder than in the case of disulfiram, though its protective potency is briefer. Other substances that can produce disagreeable reactions with alcohol include animal charcoal, the mushroom *Coprinus atramentarius*, numerous antidiabetic drugs, and the pine *Lycopodium selago*; however they have attracted very little clinical interest. Thus, in the last years, there have been an active research of other drugs to fight alcoholism without having the "disulfiram-like adverse effect", i.e., without producing disagreeable reactions with alcohol.

Many anti-alcoholism agents have been proposed, among which there are the following: opioid antagonists, such as naltrexone, naloxone and nalmefene (cf. U.S. Pat. Nos. 4,882,335 and 5,086,058); acyl L-carnitine gamma-hydroxybutyrates (cf. EP 616,805-A1), gamma-hydroxybutyric acid salts (cf. U.S. Pat. No. 4,983,632) and gamma-hydroxybutyric acid amides (cf. WO 9806690-A1); 2-pyrimidinyl-1-piperazine derivatives such as ipsapirone (cf. U.S. Pat. No. 4,895,848); pyrrolidine derivatives (cf. U.S. Pat. No. 5,935,980); cholinesterase inhibitor, such as galanthamine (cf. U.S. Pat. No. 5,932,238); serotonin reuptake inhibitors, such as fluoxetine, and the combination of the later with opioid antagonists (cf. WO 9609047-A1).

Acamprosate calcium (cf. U.S. Pat. No. 4,355,043), of formula $(CH_3-CO-NH-CH_2-CH_2-CH_2-SO_3)_2Ca$, is one anti-alcoholism agent which is being used in practice. However, it has been mentioned that the use of this compound is far from being satisfactory, and that the evidence is not strong enough to support the introduction of this substance into routine clinical practice at present (cf. Moncrieff et al., "New drug treatments for alcohol problems: a critical appraisal", *Addiction* 1997, vol. 92, pp. 939–47; discussion in pp. 949–64). Thus, apparently none of the proposed treatments of alcoholism has proved to be completely satisfactory in practice, and the pharmacological fight against alcoholism is far from being solved.

Endogenic polyamines putrescine, spermidine and spermine are compounds occurring in almost all tissues, essential for both normal and neoplastic tissue growth. They regulate DNA, RNA, and protein synthesis; stabilize ribosomes, membranes, and nucleic acids; and protect the cell against lipid peroxidation. They are metabolically related, putrescine being precursor of spermidine, and the latter precursor of spermine. These three polyamines, together with the closely related 1,3-propanediamine, are well known in chemistry.

For the treatment of alcohol and drug dependence, patent application WO 9948500 proposes the combination of an opioid antagonist (naltrexone, naloxone) with a N-Methyl-D-aspartic acid (NMDA) receptor complex modulator, particularly a spermidine site modulator such as acamprosate. However, in this document spermidine itself is neither mentioned nor suggested as an active agent for the treatment of alcoholism.

It is known that higher levels of the endogenic polyamines are found in cells that are dividing (e.g. in cancer cells) than in cells that are stable. Therefore, the concept of influencing the polyamine level in cells has been recognized and made use in chemotherapy, for example of cancerous diseases. As a consequence, these polyamines and several of their derivatives have been proposed as anti-neoplastic, anti-viral or anti-retroviral agents. Thus, for instance, patent U.S. Pat. No. 5,834,486 teaches the preparation of new substituted piperidinyl-2-alkyl linear polyamines and their use for reduction of intracellular levels of endogenic polyamines such as putrescine, spermidine and spermine. The new compounds are said to be useful for the therapeutic or prophylactic treatment of pathological conditions that are responsive to a reduction in the concentration of polyamines in cells, for example proliferative diseases, especially benign and malignant tumor diseases. Moreover, it is said that the new compounds can be used for treating protozoal infections, for example, trypanosomiasis and malaria, and opportunistic infections, such as pulmonary inflammation caused by *Pneumocystis carinii*. In this document, however, there is no mention of treatment of alcoholism. In fact, neither the endogenic polyamines themselves, nor any salt, solvate or amide thereof, have ever been proposed for the treatment of alcoholism.

SUMMARY OF THE INVENTION

The present invention relates to pharmaceutical compositions for therapeutic and/or prophylactic treatment of a patient suffering from alcoholism, having as active ingredient a polyamine of formula (I)

or a pharmaceutically acceptable salt or solvate thereof, or a physiologically-hydrolysable and acceptable amide thereof; wherein A and B radicals are the same or different from each other and are selected from the group consisting of hydrogen and —$CH_2$—$CH_2$—$CH_2$—$NH_2$; n is 3 or 4, with the proviso that when n is 3, A and B are hydrogen.

Thus, the invention also relates to a method of therapeutic and/or prophylactic treatment of a patient suffering from alcoholism, comprising the administration to said patient of an effective dose of a polyamine of formula (I), or a pharmaceutically acceptable salt or solvate thereof, or a physiologically-hydrolysable and acceptable amide thereof, together with pharmaceutically acceptable excipients or carriers.

The invention also relates to the use of a polyamine of formula (I), or a pharmaceutically acceptable salt or solvate thereof, or a pharmaceutically acceptable salt or solvate thereof, for the preparation of a medicament for the therapeutic and/or prophylactic treatment of alcoholism.

In a first embodiment, in formula (I) n is 3, and A and B are hydrogen, the anti-alcoholism agent being 1,3-propanediamine (CAS RN=109-76-2), or a pharmaceutically acceptable salt or solvate thereof, or a physiologically-hydrolysable and acceptable amide thereof. In a preferred embodiment, the anti-alcoholism agent is 1,3-propanediamine dihydrochloride (CAS RN=10517-44-9).

In a second embodiment, in formula (I) n is 4, and A and B are hydrogen, the anti-alcoholism agent being putrescine (CAS RN=110-60-1), or a pharmaceutically acceptable salt or solvate thereof, or a physiologically-hydrolysable and acceptable amide thereof. In a preferred embodiment, the anti-alcoholism agent is putrescine dihydrochloride (CAS RN=333-93-7).

In a third embodiment, in formula (I) n is 4, A is —$CH_2$—$CH_2$—$CH_2$—NHR and B is hydrogen, the anti-alcoholism agent being spermidine (CAS RN=124-20-9), or a pharmaceutically acceptable salt or solvate thereof, or a physiologically-hydrolysable and acceptable amide thereof. In a preferred embodiment, the anti-alcoholism agent is spermidine trihydrochloride (CAS RN =334-50-9).

In a fourth embodiment, in formula (I) n is 4, and both A and B are —$CH_2$—$CH_2$—$CH_2$—NHR, the anti-alcoholism agent being spermine (CAS RN=71-44-3), or a pharmaceutically acceptable salt or solvate thereof, or a physiologically-hydrolysable and acceptable amide thereof. In a preferred embodiment, the anti-alcoholism agent is spermine tetrahydrochloride (CAS RN=306-67-2).

The four polyamines included in formula (I) are chemically known, and their Registry Numbers of Chemical Abstracts Service (CAS RNs) are mentioned above. Also chemically known are some pharmaceutically acceptable salts of polyamines (I), such as their fully-neutralized hydrochlorides (i.e. their hydrochlorides with as many molecules of HCl as the number of amine groups), whose CAS RNs are mentioned above as well.

By the expression physiologically-hydrolysable and acceptable amides as used herein it is meant any amide of polyamine (I) in which one or several of its amine groups have formed amide groups with physiologically-acceptable acids, and in which said amide groups are hydrolysable under physiological conditions to yield acids which are themselves physiologically tolerable at dosages to be administered. The expression is thus to be understood as defining amides which are bioprecursor forms of compounds of formula (I), i.e., pharmaceutically acceptable biologically degradable amides of the compounds of formula (I) which, upon administration to a human being, are converted in the body to produce a compound of formula (I). Examples of such bioprecursors include amides of (I) with acetic acid, benzoic acid, benzenesulfonic acid, 4-methylbenzenesulfonic acid, and 5-(dimethylamino)-1-naphthalenesulfonic acid (or dansyl acid).

Several of the amides which are bioprecursors of the four polyamines of formula (I) are chemically known. In particular, the four fully-dansylated derivatives (i.e. the dansyl derivatives where all the existing amine groups have been converted into sulfonamide groups, here simply named "dansyl derivatives") of the four polyamines of formula (I) are chemically known and have been previously used for separation and identification of polyamine contents in association with cancer studies, partially due to their fluorescent properties. Thus, the dansyl derivative of 1,3-propanediamine (CAS RN=64144-62-3) has been prepared and used in urine analysis (cf. Abdel-Monem et al., "Polyamine metabolism. I. Synthesis of dansyl derivatives of N-(monoaminoalkyl)- and N-(polyaminoalkyl)acetamides and elucidation in urine of a cancer patient", *J. Pharm. Sci.* 1977, vol. 66, pp. 1089–94). The dansyl derivative of putrescine (CAS RN=13285-10-4), the dansyl derivative of spermidine (CAS RN=66039-59-6) and the dansyl derivative of spermine (CAS RN=66039-58-5) have also been prepared and used in the context of cancer studies (cf. Abdel-Monem et al., "Thin-layer chromatography and HPLC of the dansyl polyamines", *Adv. Polyamine Res.* 1978, vol. 2, pp. 37–49). However, none of these four dansyl derivatives has ever been associated with the treatment of alcoholism.

As illustrated by the experiments of the accompanying examples, carried out with an animal model and extrapolated to human beings, polyamines of formula (I), their pharmaceutically acceptable salts and solvates, and their physiologically-hydrolysable and acceptable amides, surprisingly cause a significant reduction in the alcohol consumption of alcoholic mammals, with a maximum effect at around 6 h after treatment, depending of the dose.

The pharmaceutical compositions of the anti-alcoholism agents of the invention can be prepared in formulations suitable for oral or parenteral administration, according to the particular requirements of the application. Oral formulations are specially preferred. As well known by persons skilled in the art, the choice of excipients in the formulations depends not only on the chemical and physical characteristics of the active principle and the required posology, but also on the type of composition desired. Besides, the dosage of the active principle obviously varies in accordance with the body weight of the patient and his clinical condition. Typical doses are those between 0.1 and 100 mg of polyamine per kg, those between 2 and 20 mg/kg being preferred.

An advantage of the present invention is that the anti-alcoholism activity of the compounds lasts for some time after the treatment period, what can allow a decrease in the dose, or even a total cure of the patient.

Another advantage of the present invention, in comparison with the unpleasant use of disulfiram, calcium cyanamide and other anti-alcoholism agents, is that the disulfiram-like adverse effect is virtually null. This probably indicates that the activity of the compounds of the present invention does not respond to a disulfiram-like mechanism of action.

The invention is illustrated by the following non-limiting examples.

EXAMPLES

Example 1

Anti-alcoholism Activity in Genetically-alcoholic Rats

As an animal model of alcoholic humans, adult Wistar rats of both sexes, belonging to the UChB strain were used. This strain of rats is the result of a long selection at the University of Chile, and rats belonging to it are known to be volunteer consumers of 10% (v/v) aqueous alcohol (cf. J. Mardones and N. Segovia-Riquelme, "Thirty two years of selection of rats by ethanol preference": UChA and UChB strains", *Neurobehav. Toxicol. and Teratol.* 1983, vol. 5, pp. 171–178). Thus, the rats used in these experiments can be considered genetically alcoholic.

Rats were kept in individual cages at 22° C., with alternative 12 h periods of light and darkness. Besides unlimited access to food, they had ad libitum access to water and 10% (v/v) aqueous alcohol. All experiments were double-blind, and results were analyzed using common statistical methods. As changes in alcohol consumption might be influenced by the eagerness of food and/or water intake, both the consumption of food and of water were measured and analyzed. However, experimental changes in the consumptions of both food and water were not significant. In each experiment the following three periods of time were considered:

a) A reference period, consisting of the three days previous to treatment. The measured consumption values were used as reference for comparison purposes.

b) A treatment period, consisting of the three days during which aqueous solutions of the tested compounds (obtained from SIGMA) were intra-gastrically administered, always at the same time of the day. Polyamines were administered as aqueous solutions of their corresponding fully-neutralized hydrochlorides, at concentration of 100 mg of the free-amine per 100 ml of water, when doses of 2 mg of amine per kg of rat; and at concentration of 1000 mg/100 ml, When doses of 20 mg/kg. Dansyl derivatives of polyamines were administered as aqueous suspensions of 100 mg of derivative per 100 ml of water, when doses of 4 mg of free-amine per kg of rat.

c) A post-treatment period, consisting of the three days immediate after the treatment period, during which measurement were taken in order to establish the duration of the effect and the reversibility of the changes.

Table 1 summarizes the average results from nine experiments, each one carried out with a set of 8 rats, where several compounds at different doses were used, and measurements of alcohol consumption were done at 6 h after the beginning of the treatment period, and at 6 h after the beginning of the post-treatment period. Figures in the table are differences in 10% (v/v) ethanol consumption between a given consumption during the reference period and the corresponding consumption during the treatment (or post-treatment) period, expressed a percentage of the consumption during the reference period (i.e. divided by this and multiplied by 100). As indicated by the figures, during treatment a significant reduction occurred in all cases; and during post-treatment a significant reduction occurred in all cases but two (those marked "ns"=non significant). Results in the table also indicate that there is a dose-effect relationship in the reduction of alcohol consumption during the treatment period. Measurements taken at 24 h after treatment (not shown in the table) indicated that, in general, the activity of the compound decreased at longer times. Other results indicated that in most cases some significant activity still lasts at the end of the post-treatment period.

TABLE 1

Reduction percentage in the consumption of alcohol (10% v/v) by genetically-alcoholic rats along the first 6 h after starting the treatment (treat.), and along the first 6 h after having stopped a 3-day treatment (post-treat.)

| Compound | dose (mg/kg) | treat. | post-treat. |
| --- | --- | --- | --- |
| 1,3-propanediamine | 20 | 27 | 12 |
| putrescine | 2 | 13 | ns |
| putrescine | 20 | 28 | 13 |
| dansyl putrescine | 4 | 23 | 22 |
| spermidine | 2 | 25 | 17 |
| spermidine | 20 | 29 | ns |
| dansyl spermidine | 4 | 29 | 19 |
| spermine | 2 | 27 | 29 |
| spermine | 20 | 42 | 12 |

Example 2

Assessment of the Disulfiram-like Adverse Effect

The disulfiram-like adverse effect of four compounds was studied by gas-chromatographic measurements of the blood concentration of acetaldehyde in standard Wistar rats, after the intraperitoneal administration of 2.76 g/kg of ethanol, administered in the form of 10% (v/v) aqueous solution. Blood samples were taken from the tail of the rat at different times after the injection of the ethanol solution. Table 2 summarizes the results from six groups of rats, each of 5 animals. The animals of the disulfiram group received two doses of 300 mg p.o. of disulfiram per kg of rat, 23 h and 17 h before the administration of ethanol. The high concentration of acetaldehyde detected in these groups was expected. The animals of the control group did not received any previous treatment. The animals of the other four groups received a single dose p.o. of 2 mg of the corresponding compound (in the form of 10 mg/100 ml aqueous solutions, which was of the hydrochlorides in the case of polyamines) per kg of rat, 1 h before the administration of ethanol. Figures in the table are mean values (±SEM) of acetaldehyde concentration in blood at the indicated times. It is observed that values of the groups corresponding to the four tested compounds were only slightly above the control ones, but far below the corresponding values of the disulfiram group. This indicates that the administration of the four tested compounds virtually does not have a disulfiram-like adverse effect. In fact, the slight effect observed after 0.5 h, virtually disappeared 2 h after the ethanol intake. Altogether, the results seem to indicate that the anti-alcoholism activity of the tested compounds does not respond to a disulfiram-like mechanism of action.

TABLE 2

Acetaldehyde concentration in blood (μg/100 ml) at different times after the injection of 2.76 g/kg of ethanol, in rats previously treated with disulfiram or with a tested compound

| Compound | 0.5 h | 1 h | 2 h |
|---|---|---|---|
| disulfiram | 725 ± 82 | 816 ± 53 | 594 ± 65 |
| putrescine | 83 ± 7 | 45 ± 6 | 35 ± 3 |
| spermidine | 138 ± 21 | 155 ± 24 | 42 ± 22 |
| dansyl spermidine | 150 ± 5 | | 40 ± 9 |
| spermine | 204 ± 4 | 50 ± 14 | 44 ± 8 |
| none (control) | 53 ± 5 | 49 ± 6 | 18 ± 5 |

The invention claimed is:

1. A method for the treatment of a human suffering from alcoholism, consisting essentially of administering to a human suffering from alcoholism an effective amount of a compound to treat said alcoholism, wherein said compound is a polyamine of formula (I)

or a pharmaceutically acceptable salt or solvate thereof, or a physiologically-hydrolysable and acceptable amide thereof, wherein A and B are the same or different from each other and are each selected from the group consisting of hydrogen and —$CH_2$—$CH_2$—$CH_2$—$NH_2$; n is 3 or 4, with the proviso that when n is 3, A and B are hydrogen; together with a pharmaceutically acceptable excipient or carrier wherein said treatment results in at least one of condition selected from the group consisting of decrease in alcohol withdrawal symptoms, reduction in development of alcohol tolerance, reduction in alcohol tolerance, reversal of sensitization to alcohol, reduction of alcohol consumption and reduction of desire for alcohol.

2. The method according to claim 1, wherein n is 3, and A and B are hydrogen, said polyamine (I) is 1,3-propanediamine.

3. The method according to claim 2, wherein the administered compound is 1,3-propanediamine dihydrochloride.

4. The method according to claim 1, wherein when n is 4, and A and B are hydrogen, said polyamine (I) is putrescine.

5. The method according to claim 4, wherein the compound is putrescine dihydrochloride.

6. The method according to claim 1, wherein when n is 4, A is —$CH_2$—$CH_2$—$CH_2$—$NH_2$ and B is hydrogen, said polyamine (I) is spermidine.

7. The method according to claim 6, wherein the compound is spermidine trihydrochloride.

8. The method according to claim 1, wherein when n is 4, and A and B are —$CH_2$—$CH_2$—$CH_2$—$NH_2$, said polyamine (I) is spermine.

9. The method according to claim 8, wherein the compound is spermine tetrahydrochloride.

10. The method according to claim 1, wherein said treatment results in at least one of condition selected from the group consisting decrease in alcohol withdrawal symptoms, reduction in development of alcohol tolerance, reduction in alcohol tolerance, reversal of sensitization to alcohol or reduction and alcohol consumption.

11. The method according to claim 1, wherein said treatment results in reduction of desire for alcohol.

* * * * *